(12) United States Patent
Byrne et al.

(10) Patent No.: US 8,163,834 B2
(45) Date of Patent: Apr. 24, 2012

(54) PHOTORESPONSIVE IONOGEL

(75) Inventors: Robert John Byrne, Dublin (IE);
Fernando Benito Lopez, Dublin (IE);
Dermot Diamond, Dublin (IE)

(73) Assignee: Dublin City University, Dublin (IE)

( * ) Notice: Subject to any disclaimer, the term of this patent is extended or adjusted under 35 U.S.C. 154(b) by 327 days.

(21) Appl. No.: 12/406,249

(22) Filed: Mar. 18, 2009

(65) Prior Publication Data
US 2010/0239647 A1 Sep. 23, 2010

(51) Int. Cl.
*C08F 222/36* (2006.01)
(52) U.S. Cl. ........... 524/548; 524/555; 524/556; 526/89
(58) Field of Classification Search .................. 252/600; 524/548, 555, 556; 526/89
See application file for complete search history.

(56) References Cited

U.S. PATENT DOCUMENTS 7,144,616 B1   12/2006   Unger et al.
7,378,168 B2    5/2008   Schumm, Jr.

OTHER PUBLICATIONS

Tamada et al. Chem. Commun., 2007, 4050-4052.*
STN Structure Search Results, Jul. 5, 2011.*
Michael J. Bassetti, Aveek N. Chatterjee, N.R. Aluru, David J. Beebe; Article Development and Modeling of Electrically Triggered Hydrogels for Microfluidic Applications; Journal of Microelectromechanical Systems, vol. 14, No. 5; Oct. 2005.
Kwang W Oh, Chong H Ahn; Article A Review of microvalves; Journal of Micromechanics and Microengineering; No. 16 (2006); R13-R39.
Douglas B. Weibel, Adam C. Siegel, Andrew Lee, Alexander H. George, George M. Whitesides; Article Pumping fluids in microfluidic systems using the elastic deformation of poly(dimethylsiloxane); The Royal Society of Chemistry Journal; No. 7, 2007, 1832-1836.
Liang Dong, Hongrui Jiang; Article Autonomous microfluidics with stimuli-responsive hydrdogels; The Royal Society of Chemistry Journal; No. 3, 2007, 1223-1230.
Shinji Sugiura, Kimio Sumaru, Katsuhide Ohi, Kazuaki Hiroki, Toshiyuki Takagi, Toshiyuki Kanamori; Article Photoresponsive polymer gel microvalves controlled by local light irradiation; online at www.sciencedirect.com, Sensors and Actuators A 140 (2007) 176-184.
Chang Liu; Article Recent Developments in Polymer MEMS; Advanced Materials Review online; Wiley-VCH Verlag GmbH&Co. KGaA, Weinheim, Germany; 2007, 19, 3783-3790.
Ernest F. Hasselbrink, Jr., Timothy J. Shepodd, Jason E. Rehm; Article High-Pressure Microfluidic Control in Lab-on-a-Chip Devices Using Mobile Polymer Monoliths; Analytical Chemistry, vol. 74, No. 19, Oct. 1, 2002, 4913-4918.
Andras Szilagyi, Kimio Sumaru, Shinji Sugiura, Thoshiyuki Takagi, Toshio Shinbo, Miklos Zrinyi, Thoshiyuki Kanamori; Article Rewritable Microrelief Formation on Photoresponsive Hydrogel Layers; 2007 American Chemical Society, published on web Apr. 28, 2007, 2730-2732.

* cited by examiner

*Primary Examiner* — David W Wu
*Assistant Examiner* — Vu A Nguyen
(74) *Attorney, Agent, or Firm* — Brown Rudnick LLP; Mark Leonardo

(57) ABSTRACT

A photoresponsive ionogel comprising a photo-responsive polymer polymerised within an ionic liquid matrix is described. This solid-state electrolyte material maintains its ionic liquid characteristics but these characteristics can be altered upon irradiation of the gel with light of a particular wavelength. By suitably configuring the ionogel through the incorporation of specific ions within the gel it is possible to cause dramatic changes in properties of the ionogel such as viscosity, conductivity, acidity, basicity and polarity using light as the stimulus.

1 Claim, 8 Drawing Sheets

X:Y:Z = 1:99:5

PHOTORESPONSIVE IONOGEL

FIELD OF THE INVENTION

The present invention relates to ionogels which in the context of the present teaching may be considered a solid state electrolyte material comprising ionic liquids. The invention more particularly relates to photoresponsive ionogels, i.e. ionogels whose properties may be modified on irradiation to light.

BACKGROUND

Ionic liquids (ILs) are currently the focus of a rapidly growing number of studies in materials science. Within the present specification "ionic liquid" includes those salts whose melting point is below 100° C. Within this context salts that are liquid at room temperature are called room-temperature ionic liquids and typically comprise an organic cation. ILs were first studied for electrometallurgy, high-temperature batteries and organic synthesis, for their wide electrochemical windows, ionic conductivity, good chemical and thermal stability, very low volatility, solvent properties and broad liquid range over room temperature. Since then, their design has been rationalized for specific tasks in organic synthesis and catalysis, in green chemistry, and in energy production and storage as electrolytes. Increasingly, numerous studies are currently stemming from some early hints regarding their use in materials science, for instance as lithium batteries, supercapacitors, solar and fuel cells.

Besides the goal of taking advantage of the properties of ILs in materials, their liquid nature limits their use due to shaping necessities in most devices as a result of possible leakages and miniaturization impediments. Thus, regardless of the pursued application, taking advantage of IL properties in solid-state materials remains a major challenge. To this aim, several approaches are under investigation through grafting on supports, swelling in polymers and impregnation on preliminary prepared oxide particles. Despite these research fields there are still problems associated with stabilization of ionic liquids within a solid form.

For these reasons and others there is a need for ionic liquids in stabilised forms.

SUMMARY

These and other problems are addressed by an ionic liquid that is stabilised in a gel format. The gel may be considered a solid-state material. The combination of the ionic liquid in the gel forms a hybrid material. In a preferred arrangement the gel is a photoresponsive gel such that the resultant hybrid material is a photoresponsive ionogel. Such a solid state electrolyte material maintains its ionic liquid characteristics but these characteristics can be altered upon irradiation of the gel with photons. By suitably configuring the ionogel through the incorporation of specific ions within the gel it is possible to tune the photo-rheological properties of the ionogel so as to have one or more desired properties such as viscosity, conductivity, acidity, basicity and polarity.

Accordingly an ionogel as claimed in claim 1 is provided. Advantageous embodiments are provided in the dependent claims. A solar cell comprising an ionogel is also provided. A fabric comprising an ionogel is also provided. A microvalve comprising an ionogel is also provided.

These and other features of the present teaching will be understood with reference to the exemplary arrangements which follow which are provided to assist in an understanding of the present teaching but are not to be construed as limiting the present teaching to that described.

BRIEF DESCRIPTION OF THE DRAWINGS

The present invention will now be described with reference to the accompanying drawings in which.

DETAILED DESCRIPTION OF THE DRAWINGS

The teaching of the present invention will now be described with reference to exemplary arrangements thereof. These arrangements will be described with reference to photo-rheological materials based on stabilizing an ionic liquid within a gel to form a photo-responsive ionogel. Such a photo responsive ionogel may be used in a variety of different applications including for example drug delivery systems, permeable membranes, microvalves and actuators. By providing a photo-responsive material it is possible to apply photonic control to that material. Such control is a useful and important means of control because it can be applied instantaneously and with high spatial resolution, without physical contact. A photo-responsive ionogel fabricated in accordance with the present teaching is resultant from combination of a polymer blend with an ionic liquid (IL) to create a superior hybrid material for advanced functions.

While the teaching is not to be construed as being limited to any one specific form of a photo responsive ionogel, fabrication of an exemplary material will now be described. Such a material may be fabricated from poly(N-isopropylacrlamide) (pNIPAAM), which is a well-known thermoresponsive polymer. In water, pNIPAAM gels undergo a volume phase transition at their lower critical solution temperature (LCST), around 34° C., which can be substantially affected by modifying the chemical structure of the polymer network by copolymerization.

Figure 1:
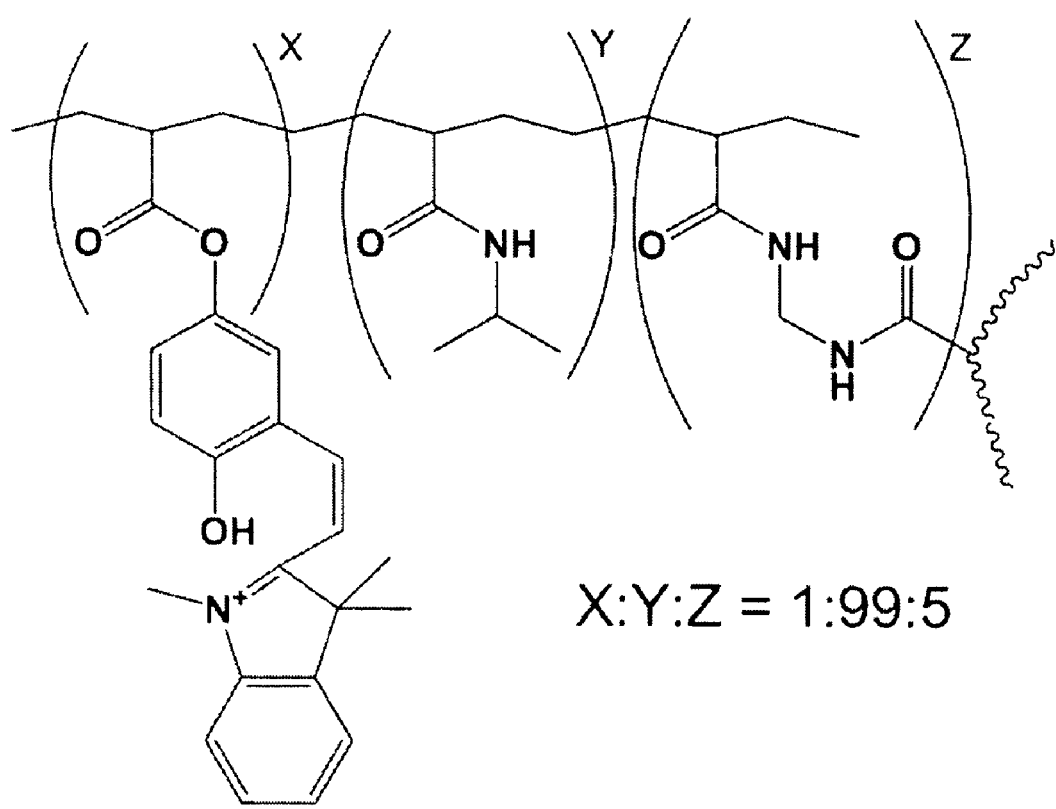
FIG. 1 is an example of an ionogel comprising poly(N-isopropylacrylamide), N,N-methylene-bis(acrylamide) and acrylated benzospiropyran.

In this exemplary arrangement three monomeric units; poly(N-isopropylacrlamide), N,N-methylene-bis(acrylamide) and acrylated benzospiropyran were combined in the ratio 100:5:1, respectively. An example of the final structure is shown in FIG. 1. The acrylated benzospiropyran may be synthesized in a form such as described in Szilagyi, A.; Sumaru, K.; Sugiura, S.; Takagi, T.; Shinbo, T.; Zrinyi, M.; Kanamori, T. *Chemistry of Materials* 2007, 19, 2730-2732. The benzospiropyran is exemplary of a photochromic moiety whose colour will change in response to light. Photochromism may be simply defined as a light-induced reversible change of colour and a more precise definition and examples of other moieties which are photochromic may be found in ORGANIC PHOTOCHROMISM (IUPAC TECHNICAL REPORT) Pure Appl. Chem., Vol. 73, No. 4, pp. 639-665, 2001 The benzospiropyran molecule comprises a free double bond and its isomeric state changes from cis to trans on radiation.

Figure 2:
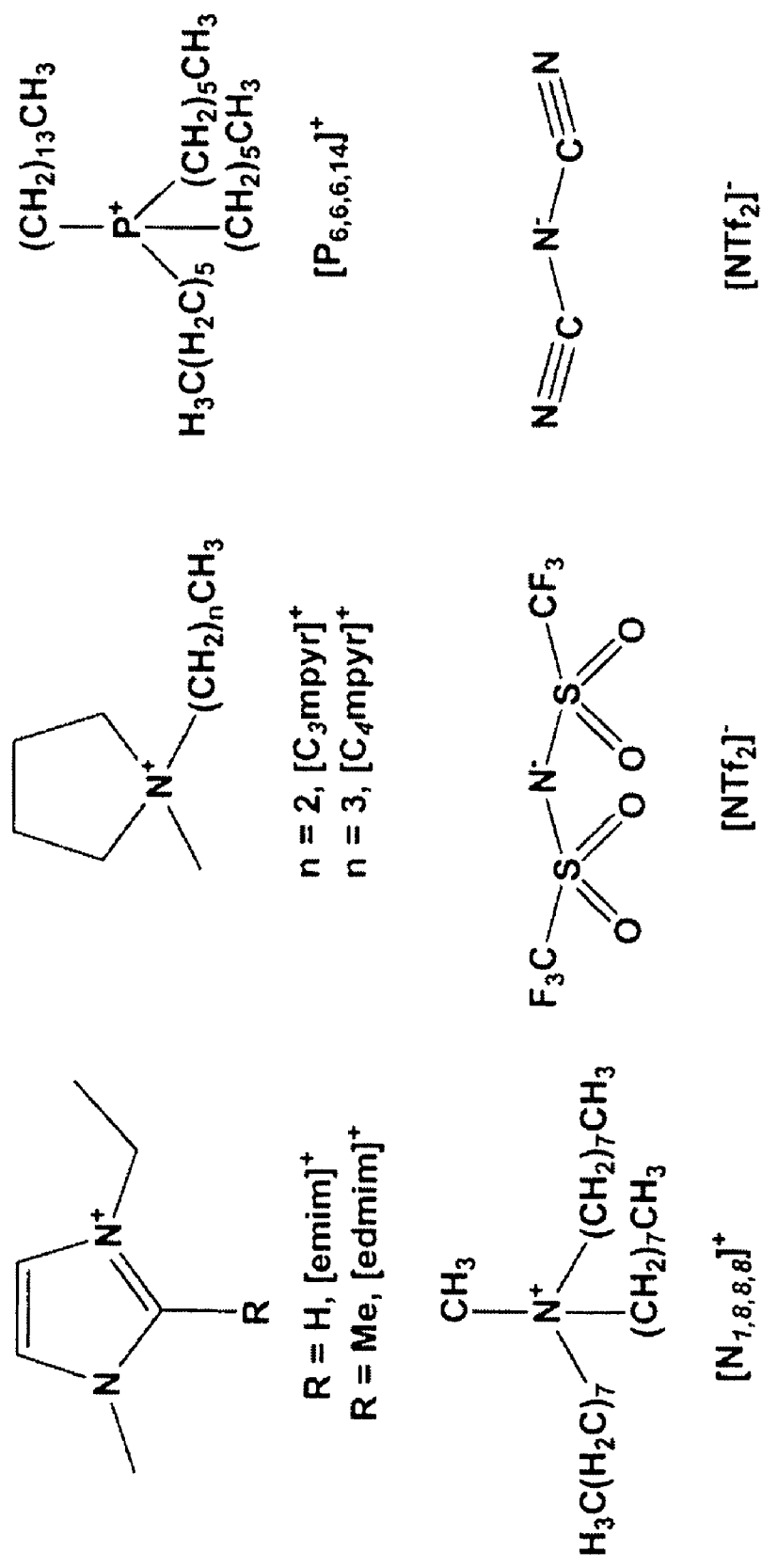
FIG. 2 shows examples of molecular structures of cations and anions used as support matrix within ionogel: ethyl methyl imidizolium [emim]$^+$, ethyl dimethyl imidizolium [emim]$^+$, N-propyl N-methyl-pyrrolidium [C$_3$mpyr]$^+$, N-butyl N-methyl-pyrrolidium [C$_4$mpyr]$^+$, trihexyltetradecylphosphonium [P$_{6,6,6,14}$]$^+$, trioctyl, methyl ammonium [Oct$_3$NMe]$^+$, bis(trifluoromethanesulfonyl) amide [NTf$_2$]$^-$ and dicyanoamide [dca]$^-$

The monomers are photo-polymerized within an ionic liquid matrix using the photo-initiator DMPA (1 mol%). For this example, the ionic liquid matrix used was trihexyltetradecylphosphonium dicyanoamide $[P_{6,6,6,14}][dca]$ ionogel washed with ethanol/water to remove un-reacted monomers. After washing, the ionogel was immersed within 1 mM HCl solution. At this stage, containing 0.1 mM HCl. Physical and chemical characteristics of the ionogel can be modified by the incorporation of different ionic liquids such as those described in FIG. 2. It will be appreciated that ionic liquids (ILs) are organic salts in the liquid state at ambient conditions and many show negligible volatility and non-flammability. The advantage of impregnating the photoresponsive gels with ILs over aqueous media is the possibility to tailor the properties of the gels (polarity, viscosity etc.). Therefore, it is possible within the context of the present teaching to prepare many photoresponsive gels with particular characteristics by substituting the appropriate IL.

It will be appreciated that the provision of a hybrid material comprising three monomeric components polymerized within an ionic liquid yields a photo-rheological ionogel. Photo-irradiation of such an ionogel with the appropriate wavelength of light results in three dramatic changes in the materials properties. Firstly, the ionogel volume decreases dramatically. Secondly, upon photo-irradiation we observe the release of a highly acidic proton. Thirdly, as a result of the previous two effects, the electrochemical properties of the ionogel can be altered by photons. More importantly, these effects are completely reversible by removal of the irradiation source.

The mechanism of actuation in this specific example is achieved through the photoisomerization of the acrylated benzospiropyran within the ionogel. As the ionogel at equilibrium is in a hydrophilic state, it retains molecular $H_2O$, upon irradiation benzospiropyran isomerizes into a hydrophobic molecule, resulting in conformational change of the ionogel expelling $H_2O$ thus altering the materials properties.

Figure 3:
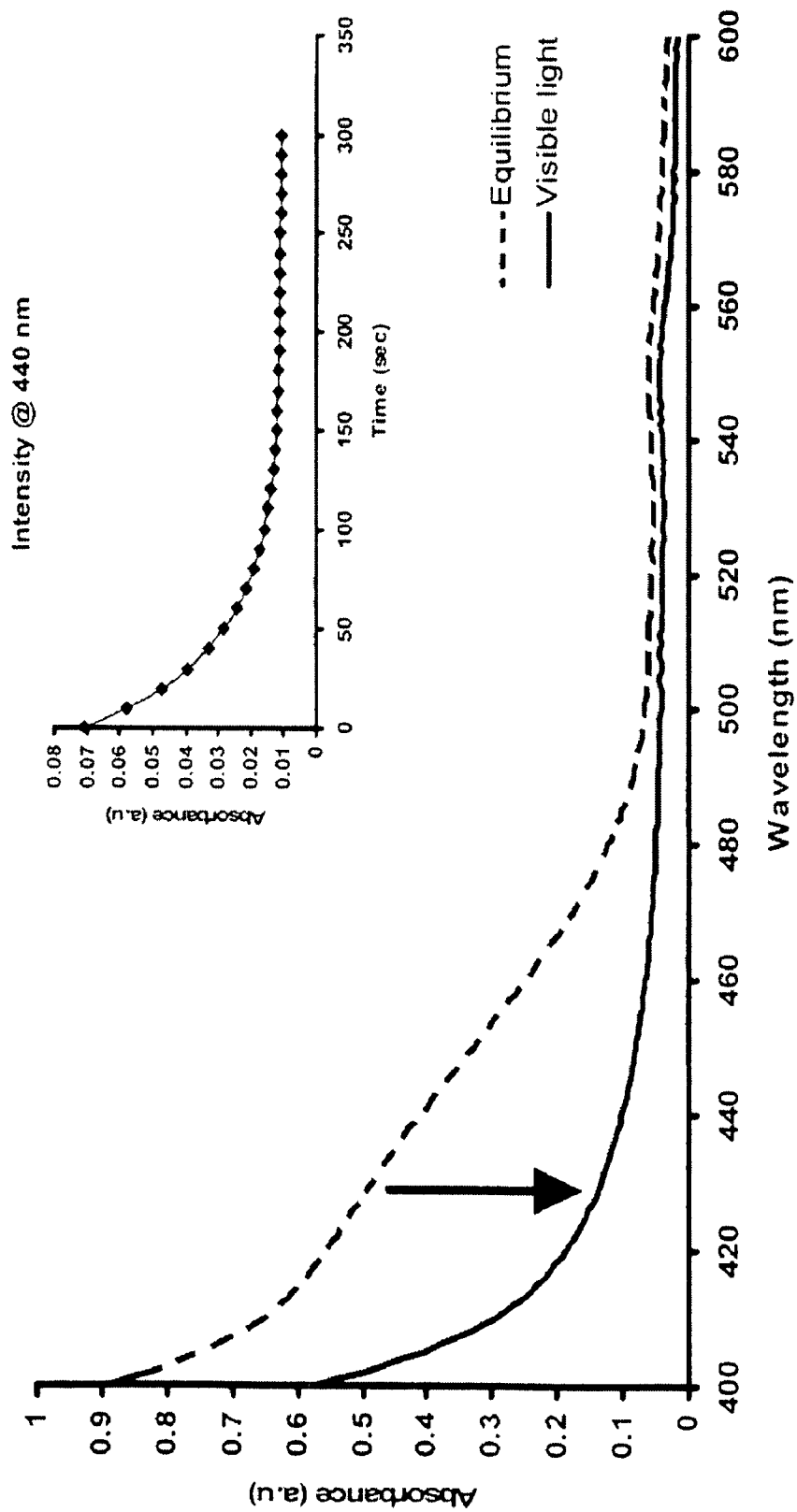
FIG. 3 shows a UV-Vis response of a prepared ionogel at equilibrium and the response after 60 s exposure to visible light. The inset shows a first order kinetic plot of absorbance decay at 440 nm with visible light irradiation.
Figure 4:
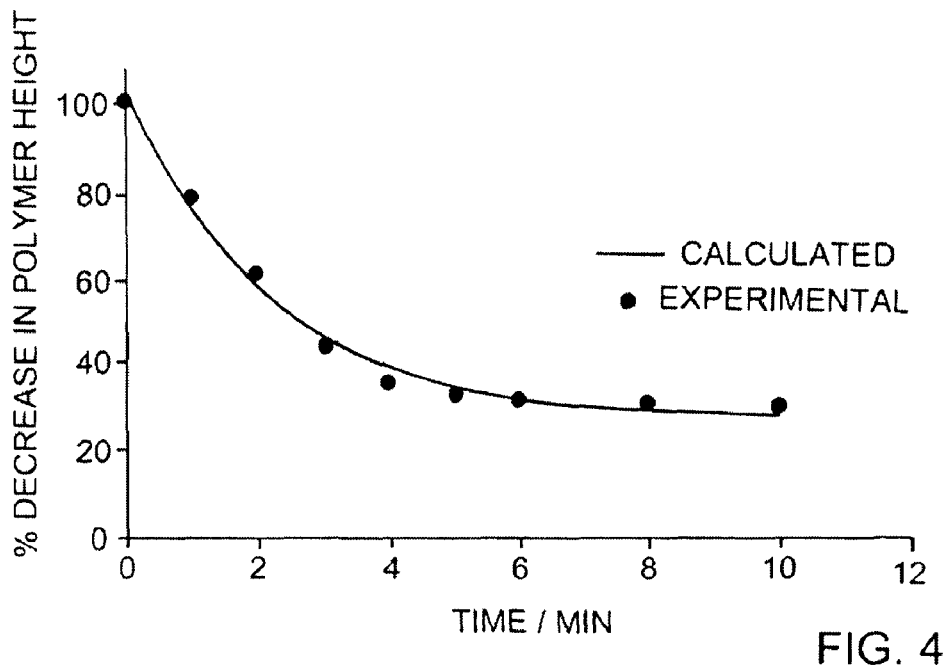
FIG. 4 shows polymer shape and colour change when visible light is applied, the kinetic constant calculation using a physical contact profilometer
Figure 5:
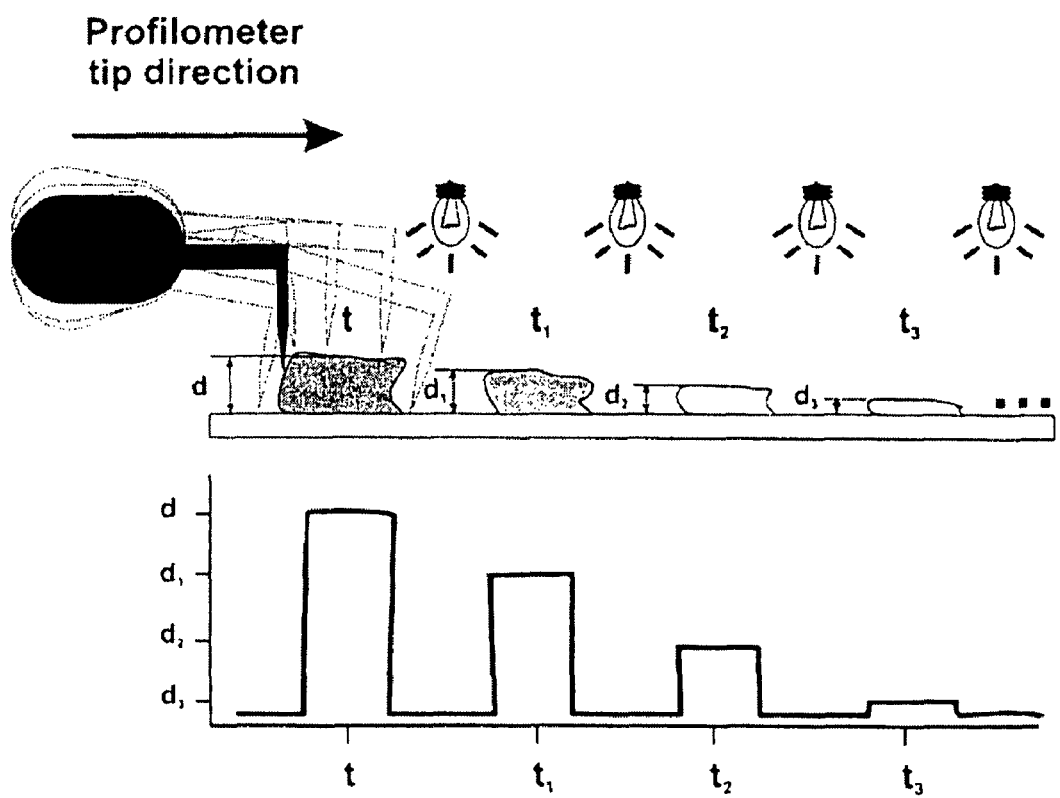
FIG. 5 shows an example of a schematic representation of the set-up used for the profilometer measurements of FIG. 4.

It is possible to characterise the properties of this hybrid material. UV-Vis analysis of the ionogel at equilibrium, such as that shown in FIG. 3, indicates the presence of protonated form of the merocyanine due to the band at 440 nm. Upon exposure to visible light, the band at 440 nm decreases in intensity due to the ring closing of the merocyanine (hydrophilic) and conversion to the spirobenzopyran (hydrophobic) form. This ring closing induces a dehydration of the ionogel due to expulsion of the creation the acidic proton generating a much more hydrophobic environment. Ring closing kinetic rate constant calculated to be $2.5 \times 10^{-2}$ s$^{-1}$ Irradiation by the light source effects a photo-induced dehydration of the material which causes a physical shrinkage of the ionogel, as seen in the images within FIG. 4. After 150 seconds of visible light, there is a 73% decreasing on the ionogel height. This photo-effect was monitored using a physical contact profilometer, such as that shown in FIG. 5 with the resultant kinetic rate of shrinkage being estimated as 0.457 s$^{-1}$.

Figure 6:
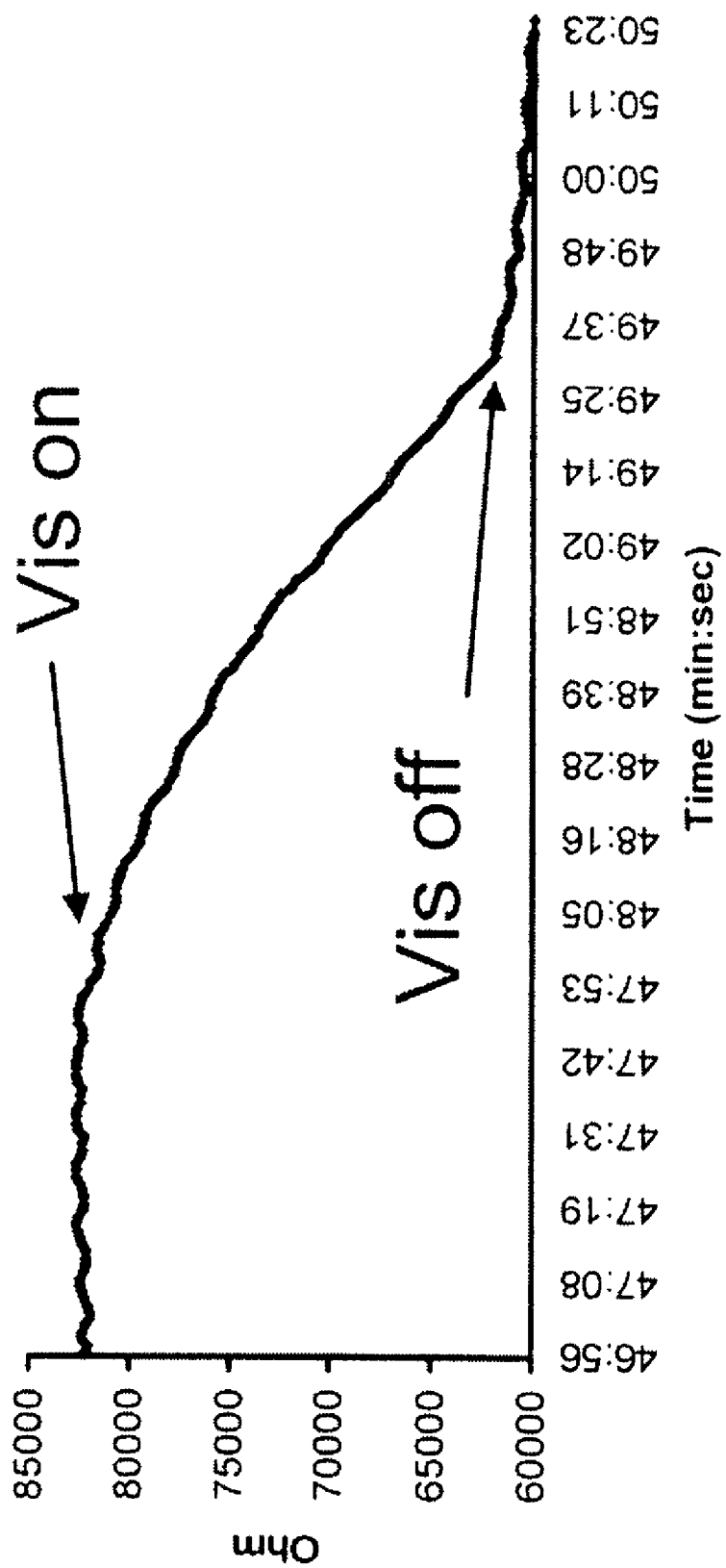
FIG. 6 shows how the electrical resistance of ionogel decreasing upon irradiation of visible light

In addition to the modification of the physical characteristics of the gel, the photo-irradiation can also be used to modify the electronic and electro-chemical properties of the ionogel, as demonstrated in FIG. 6 with the measurements being carried out in AC mode. It is evident that upon irradiation of light, electrical resistance decreases by 25%.

A hybrid material whose electrical and physical characteristics can be modified on irradiation has a number of different applications, of which a number of exemplary applications follow.

EXAMPLE 1

Figure 7:
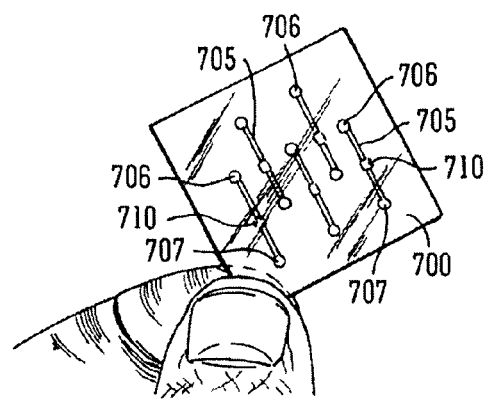
FIG. 7 shows an example of a fabricated PDMS:PSA microfluidic device comprising a plurality of individual channels.

Fabrication of PMMA:PSA Microfluidic Devices Incorporating Photo-Responsive Ionogel Based Valves It is possible in accordance with the present teaching to fabricate a microchip. An example of such a microchip 700 is shown in FIG. 7. In this exemplary arrangement the dimensions provided are of a 4×4 cm device but it will be appreciated that other dimensions can be easily also fabricated in accordance with the present teaching. In the exemplary arrangement of FIG. 7 the chip 700 comprises five channels 705, each channel having a liquid source 706 and destination 707 separated by a photoresponsive valve 710. The valve is provided within a channel and serves to isolate the source from the destination. Each channel could be independently operated and use of such a chip will be described with reference to FIG. 9 below.

Figure 8:
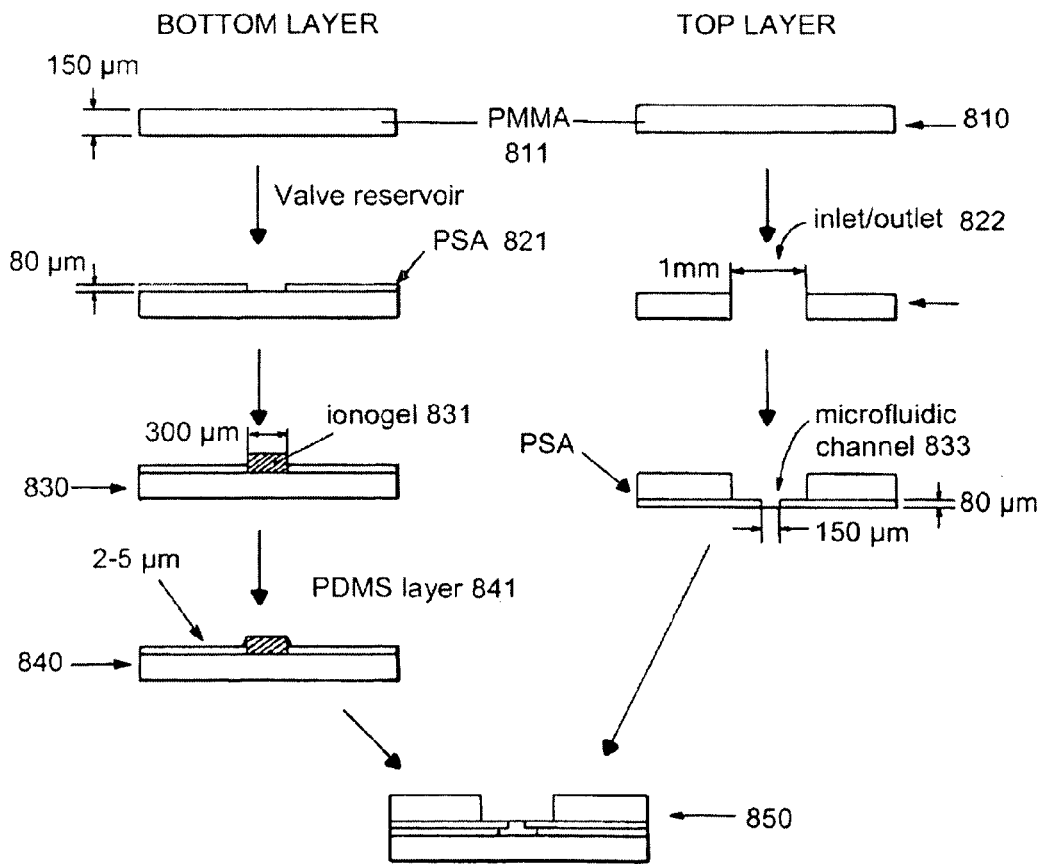
FIG. 8 shows exemplary steps that may be followed to fabricate a device such as that shown in FIG. 7.

As will be apparent from the schematic of FIG. 8 which follows such an arrangement may be provided in a multilayer structure based on poly(methyl methacrylate) (PMMA) and pressure sensitive adhesive (PSA) as base materials. In the exemplary arrangement of FIG. 7, five separate microchannels 710 are concurrently provided on the same device.

As shown in FIG. 8, in-step 810 bottom and top layers of PMMA 811 are provided. On the bottom layer a PSA layer 821 is immobilised on the upper surface 810. The PSA layer is immobilised according to a template that will define the ultimate positioning of the ionogel. The top layer is etched using for example a $CO_2$ laser to form an inlet/outlet 822 for the final device.

In Step 830 the ionogel 831 (which will ultimately define the valve element of the device) is placed in a square reservoir, fabricated using the CO2 laser, within the PMMA (125 μm) and PSA layer (80 mm deep, 300 mm width/length) on the bottom layer. A second PSA layer with the channel structures (80 μm deep, 150 μm width, and 20 mm length) is fabricated using the CO2 laser and terminally glued to the previous one on the top layer.

In Step 840 the ionogel is then covered with a thin and flexible PDMS layer 841 for isolation purposes thus microvalves are physically independent of the microfluidic channel, nevertheless tuning the ionogel properties, e.g. hardness, flexibility, this PDMS layer is not strictly necessary. Microvalves can be relocated simply by varying the layer layout.

Finally in Step 850, the upper PMMA layer, which contains the inlets and outlet, closes the microchip structure.

A microreactor valve fabricated in accordance with FIG. 8, was successfully tested using vacuum as driving force through the outlet and a coloured dye solution at the the inlet. The inlet corresponds with the source 706 and the outlet with the destination 707 discussed above with reference to FIG. 7.

Figure 9A:
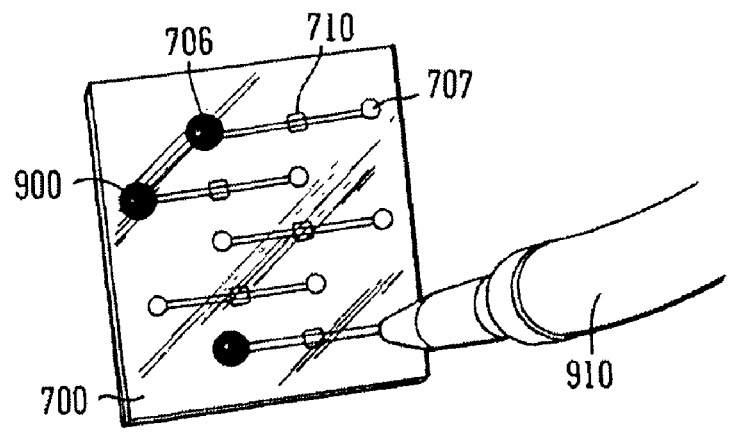
FIG. 9 shows the operation of a microfluidic valve as provided using a photoresponsive ionogel in accordance with the present teaching.
Figure 9B:
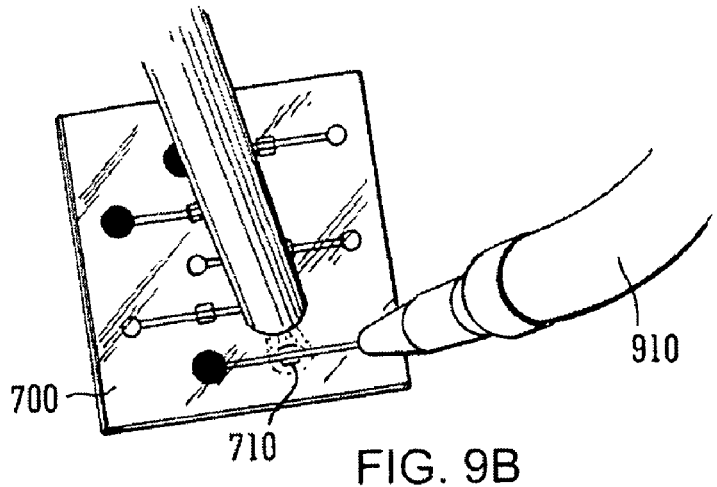
Figure 9C:
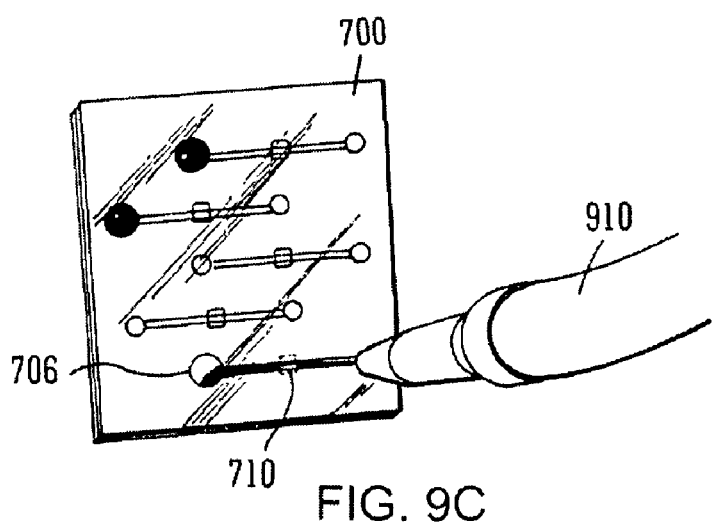

When light is applied to the valve 710 the polymer decreases in volume and so the valve opens letting the colorant, which is a fluid 900, pass through the channel 705 from the source to the destination. Examples of the response are shown in FIG. 9 where FIG. 9A shows the microvalve in a closed orientation. In this mode, the vacuum is unable to draw the dye solution 900 through the microchannel. In FIG. 9B, white light is applied using a light pen 910 which effects an opening of the microvalve 710. FIG. 9C shows how with the valve open, the vacuum is capable of draw the dye solution 900 through the microchannel such that it extends from the source 706 through the channel 705 towards the destination outlet.

It will be appreciated that a microdevice such as that shown in FIGS. 7 through 9 offers a number of advantages over prior art arrangements. Such a device incorporates a photoresponsive ionogel which provides the function of a valve to control the flow of a liquid through the device, with the result that fluids in the chips are easily controlled by simply applying light to the ionogel incorporated as valves in the channel structures. As the valve does not require physical contact for operation there is no need for any external controller or actuator to be operated.

These valves are reversible and can be reusable many times. By simply changing the lighting conditions to which the valve is exposed it is possible to change the operating performance of the device.

It is extremely easy to fabricate such devices with the result that these offer a cost effective solution with mass production fabrication available at low cost.

It will be appreciated that as the performance of the device is dependent on the location of the ionogel that such devices are very versatile and their application can be modified by simply changing the location of the ionogel relative to other components of the device.

It will be understood that such devices have therefore widespread application in autonomous microfluidic systems. Such systems are rapidly gaining momentum in the, fields of analytical science and biotechnology and they are the essential component in portable and point of care analysis systems. They consist of a network of microchannels which also require micropumps, valves, and mixers to control fluid movement throughout the network. Conventional solid-state actuators and valves such as pumps (e.g. piston, peristaltic, syringe-based etc.) and solenoid valves are costly, require significant power and are fundamentally difficult to downscale and integrate into the microfluidic platform, which limits their use in many microfluidic applications. For example, valves, must be closely integrated to the microchannels to minimise dead volumes, and conventional micromachined hard materials/surfaces used in micropumps and valves are very susceptible to microparticulates that tend to make this approach fundamentally unreliable. Current microfluidic valves often contain membrane assemblies which often are not resistant against high pressure.

However by employing photoresponsive devices such as those provided in accordance with the present teaching it is possible to provide low-cost, efficient, soft-polymer based actuators and valves for sample handling in microfluidics systems. The optical-triggering or actuation of these embedded microstructures is particularly attractive, as electronic actuation requires specific interconnects, cables, wires and direct physical contact between the stimulus (conductor) and the polymer actuator. In contrast, as highlighted above photoresponsive ionogel in accordance with the present teaching can be easily incorporated as a valve in a microfluidic system, and the material can be completely embedded within the manifold, with no need for external connections to circuitry or power sources.

EXAMPLE 2

Flow Controller in Catheters, Capillaries and Small Pipes

Figure 10A:
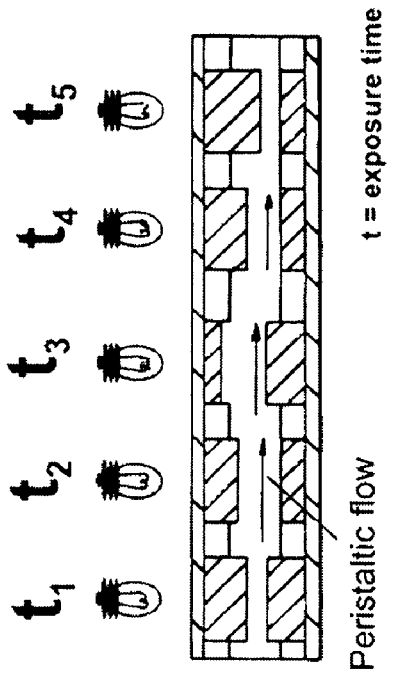
FIG. 10A shows a silica capillary coated with an ionogel and FIG. 10B shows peristaltic flow generation using a LED array acting on such a capillary.
Figure 10B:
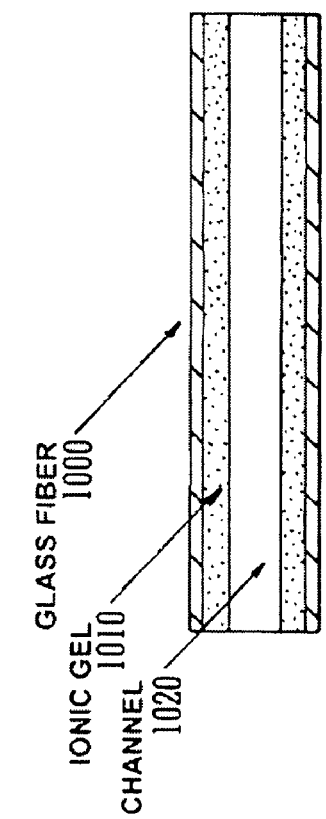

Such devices can also be used to control the amount of liquid and its flow rate through a capillary by the actuation generated by these ionogels when coated on the capillary surface. Different wavelengths of light could be applied simultaneously to generate a peristaltic flow regime. An example of such an arrangement is shown in FIG. 10. In FIG. 10A a silica capillary 1000 is coated with ionogels 1010 and a channel 1020 is defined. The coating can be easily performed by for example photo-polymerization of the ionogel in the capillary surface that has been previously activated with NaOH and pre-coated with 3-(trimethoxysilyl)propyl methacrylate. (Such an analogous procedure is used in creating monoliths in capillaries, discussed for example in J. Sep. Sci. 2007, 30, 3060-3068).

The ionogel may be tailored to different wavelengths through the fabrication process. When only one light is applied to a defined polymer area; an aperture will be generated modifying the flow regime when liquid is externally introduced into the capillary. In general terms, this principle could be used for controlling the amount of liquid which is needed to be transfer from one container to another in a precise way by use of a pseudo peristaltic effect. Some applications are: chemical reactions synthesis and kinetic studies or medical application in controlling the injection of different drug gradients into the body via external catheters in hospitalized patients (for example in chemotherapy treatments).

As the ionogel is provided in a solid form, its controlled deposition at specific points on a surface is possible. The use of two or more different ionogels, differing in their optical response characteristics can be used to define within a single channel different regions with different response characteristics. In this way controlled flow through a substrate or other fluid path may be defined using selective exposure to light of specific wavelengths—i.e. only certain valves open on exposure to specific radiation (wavelength addressable). This could also be used to control the flow to multiple destinations by opening specific flow paths within a structure using specific light wavelengths to actuate specific valves. With a plurality of valves arranged along a longitudinal path it is possible to selectively actuate individual ones, or sets of, valves to induce and control the flow of a liquid through that path.

EXAMPLE 3

Drug Delivery System

By providing a photoresponsive device which on exposure to light of specific wavelengths it is possible to enable controlled drug delivery—especially where the drug is provided in a fluid form. For example one of the major goals in drug delivery is in controlling insulin dosage for diabetics; replacing injection-based delivery of insulin with a more passive method is obviously very desirable for patients. Some attempts have involved:
1) implantable or externally worn insulin pumps which are cumbersome devices, attached to body, and require a direct opening into a blood vessel which invariably leads to infection;
2) inhalation of insulin which still have questions regarding long-term use of inhalers irritating the lungs and whether they be effective in a person with a cold or other respiratory disorder; and
3) transdermal patches. A transdermal patch or skin patch is a medicated adhesive patch that is placed on the skin to deliver a specific dose of medication through the skin and into the bloodstream. In diabetes, the issue of controlling the release of insulin is extremely important as insulin is needed to break down the sugars ingested. If the patient's transdermal patch has not delivered sufficient insulin to the body they run the risk of serious health problems. Some researchers have produced a watch-like device that tests for blood glucose levels through the skin and administers corrective doses of insulin through pores in the skin, although these microfluidic systems suffer from all the drawbacks mentioned above with regard to externally worn pumps.

Figure 11:
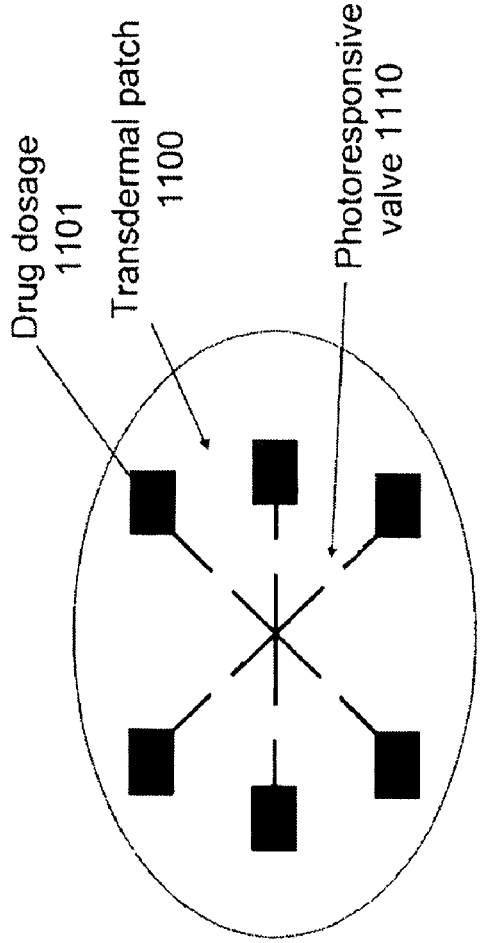
FIG. 11 shows a transdermal patch incorporating a photoresponsive valve as provided in accordance with the present teaching.

In accordance with the present teaching a photo-responsive ionogel may be used in a photo-actuated transdermal device. An example of such a transdermal device 1100 is shown in FIG. 11 and may be used to deliver specific dosages of a drug 1101 such as insulin by irradiation with a certain wavelength of light. By allowing user control of the delivery and controlling that delivery by means of a photoactuated microvalve 1110—it is possible to provide an effective, low-cost and passive drug delivery system. Furthermore, the dosage can be released under user control via an instrument such as a LED-based light pen, or alternatively, the patch can be completely autonomous, with the drug release being triggered via one or more light emitting diodes (LEDs) embedded within the patch.

EXAMPLE 4

Solar Cell Technology

Dye-sensitized solar cells (DSSCs) have attracted great attention over the past decade due to their high photo-energy conversion efficiencies and low cost cell fabrication processes. For DSSCs, the electrolytes usually consist of an iodide/triiodide redox couple in organic solvents. However, the disadvantages of using liquid electrolytes are less long-term stability, difficulty in robust sealing, evaporation and leakage of electrolyte in case of breaking of the glass substrates. An ionogel stabilizing ionic liquid such as that provided within the context of the present teaching could be used an electrolyte in such DSSC's. Such an ionogel material has all the attributes needed for a solid sate DSSC; non-crystalline polymer, room temperature ionic liquid (RTIL), and photochromic moiety. By providing an electrically responsive material whose characteristics depend on the incident radiation it is possible to provide the necessary response characteristics to provide a DSSC.

EXAMPLE 5

Smart Textiles (Textile Porosity and Permeability)

The fundamental role of clothing is to keep us warm or cool with the result that there are a number of developments in fabric and textiles relating to regulation of body temperatures. In the sector, there is considerable interest in so-called 'phase-change fabrics', particularly as heat-modifying textiles applied mainly to outdoor activities. As the body temperature increases, due to direct sunlight, these materials become more liquid in form and heat transfer properties are enhanced, enabling heat to be more effectively transferred to external layers, which increases the cooling effect of the textile. On the other hand, when external temperatures drop, due to lack of sunlight, these materials solidify, and heat retention within the material is enhanced, reducing the loss of body heat to the external environment.

As will be appreciated from the above discussion an ionogel provided in accordance with the present teaching may be fabricated using NIPAAm. Such a polymer is light sensitive and by suitable treatment could be fabricated into a fabric suitable for incorporation into woven or other formed textile based products. This incorporation could be by crosslinking the ionogel into the fabric of the material or incorporating it covalently to form an integral part of the fabric. In this way it would be possible to incorporate it into a fabric as an air conditioning component. It is possible to modify the polymer NIPAAm phase transition temperature by modifying the chemical structure of the polymer network by copolymerization, therefore it would be possible to tune phase changes occurring in the material to to specific intensities of sunlight.

CONCLUSION

It will be appreciated that what has been described herein are exemplary arrangements of a photo-responsive ionogel. Such a device or component takes advantage of two base properties—molecular photoswitching & ionic liquids. By combining materials that have these specific properties the present inventors provide a synergistic effect whereby the dissolving of photoswitches within ionic liquids provides an enhancement in switchable behaviour, and improvement in the operational characteristics, for example, in the photoactuation behaviour of the resulting ionogels. This goes far beyond the typical advantages often quoted for using ionic liquids in preference to standard solvents, such as lack of volatility, ease of synthesis, libraries of potential liquids available, variability and tuneability of fundamental properties (polarity, acidity etc.). While it is not intended to limit the present invention to any one underlying theory, it is believed that this synergy between the ionic liquids and the photoresponsive gels arises from specific molecular interactions between the ionic liquid constituents and the photoswitches, that go beyond a simple solvent-solute relationship.

Accordingly while the present invention has been described with reference to exemplary arrangements thereof, it will be understood that modifications can be made without departing from the scope of the present teaching. The teaching of the present invention is to be construed as limited only as is deemed necessary in the light of the appended claims which follow.

The words comprises/comprising when used in this specification are to specify the presence of stated features, integers, steps or components but does not preclude the presence or addition of one or more other features, integers, steps, components or groups thereof.

The invention claimed is:
1. A microvalve comprising a photo-responsive polymer that was polymerized within an ionic liquid matrix so as to form a photoresponsive ionogel, operable exposure of the ionogel to light effecting an opening or closing of the microvalve, and wherein the photo-responsive polymer is formed by the reaction of(N-isopropylacrylamide), N,N-methylene-bis(acrylamide) and the protonated form of 1',3',3'-trimethyl-6-acrylate(2H-1-benzopyran-2,2'-indoline) monomers provided as first, second and third polymer components having a structure

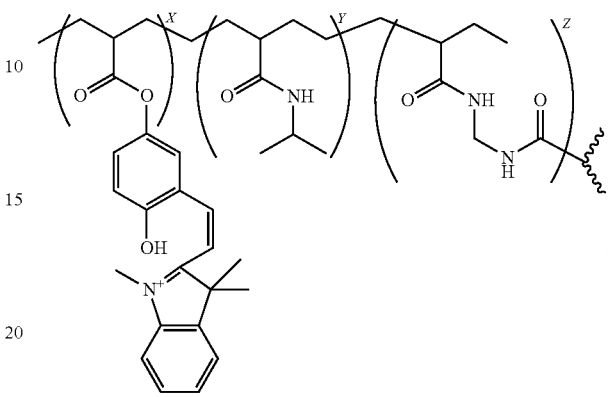

X:Y:Z = 1:99:5

* * * * *